United States Patent
Hall et al.

(10) Patent No.: US 9,993,161 B1
(45) Date of Patent: Jun. 12, 2018

(54) EXCREMENT-BASED BODY TEMPERATURE MEASUREMENT DEVICE

(71) Applicants: David R. Hall, Provo, UT (US); Dan Allen, Springville, UT (US); Cameron Price, Provo, UT (US)

(72) Inventors: David R. Hall, Provo, UT (US); Dan Allen, Springville, UT (US); Cameron Price, Provo, UT (US)

( * ) Notice: Subject to any disclaimer, the term of this patent is extended or adjusted under 35 U.S.C. 154(b) by 97 days.

(21) Appl. No.: 15/367,591

(22) Filed: Dec. 2, 2016

(51) Int. Cl.
*A61B 5/01* (2006.01)
*G01J 5/34* (2006.01)
*G01J 5/00* (2006.01)
*A47K 13/24* (2006.01)
*E03D 11/13* (2006.01)
*A61B 5/00* (2006.01)

(52) U.S. Cl.
CPC .............. *A61B 5/01* (2013.01); *A47K 13/24* (2013.01); *A61B 5/0082* (2013.01); *A61B 5/6887* (2013.01); *E03D 11/13* (2013.01); *G01J 5/0003* (2013.01); *G01J 5/0025* (2013.01); *G01J 5/34* (2013.01)

(58) Field of Classification Search
CPC .............................. A61B 5/01; A61B 5/0082
See application file for complete search history.

(56) References Cited

FOREIGN PATENT DOCUMENTS

CN 205975865 U * 2/2017

* cited by examiner

*Primary Examiner* — Casey Bryant (57) ABSTRACT

Body temperature of a toilet user may be non-intrusively obtained on a regular basis using one or more non-contact optical temperature sensors having a field-of-view between a surface of a toilet bowl and a user of the toilet while the user is releasing body excrement into the toilet. An output of the non-contact optical temperature sensor is used to determine a body temperature of the user based on at least one of: a temperature of the body excrement while the body excrement is in the field-of-view of the non-contact optical temperature sensor, a temperature of a perineal area of the user while using the toilet, a temperature of the body excrement while the body excrement is detached from the body and falling toward the surface of the toilet bowl, or a combination thereof.

19 Claims, 10 Drawing Sheets

EXCREMENT-BASED BODY TEMPERATURE MEASUREMENT DEVICE

BACKGROUND

Field of the Invention

The present invention relates to the measurement of body temperature using human excrement.

Background of the Invention

Non-contact temperature sensors are well known for measuring temperatures of objects at a distance. Fast response and high accuracy non-contact temperature devices are manufactured by Fluke, Omega, and FLIR.

For management and detection of various health conditions, it is useful to track body temperature in non-intrusive and regular intervals.

SUMMARY

By using a toilet temperature measurement device, it is possible to determine a body temperature of a toilet user based on a temperature profile of feces produced by the user. Body excrement can be measured at multiple points by a non-contact optical temperature sensor allowing a body temperature of a user to be accurately determined.

Body temperature of a toilet user may be non-intrusively obtained on a regular basis using one or more non-contact optical temperature sensors having a field-of-view between a surface of a toilet bowl of a toilet and a user of the toilet while the user is releasing body excrement into the toilet. An output of the non-contact optical temperature sensor is used to determine a body temperature of the user based on at least one of: a temperature of the body excrement while the body excrement is in the field-of-view of the non-contact optical temperature sensor, a temperature of a perineal area of the user while using the toilet, a temperature of the body excrement while the body excrement is detached from the body and falling toward the surface of the toilet bowl, or a combination thereof.

An excrement-based body temperature measurement device may include one or more non-contact optical temperature sensors. The non-contact optical temperature sensors may be used to determine a surface temperature of body excrement as it exits a toilet user's body or falls from the toilet user's body into water in a toilet bowl. One or more non-contact optical temperature sensors may be mounted on a toilet seat of a toilet. One or more of the non-contact optical temperature sensors may be mounted in a toilet bowl. The non-contact optical temperature sensors may have a field of view which is below a plane of the toilet seat. The non-contact optical temperature sensors may have a field of view below a rim of the toilet bowl. The non-contact optical temperature sensors may be thermal imaging sensors. The non-contact optical temperature sensors may use a medium wavelength infrared camera. The non-contact optical temperature sensors may use a long wavelength infrared camera. The non-contact optical temperature sensors may use a visible light camera. The non-contact optical temperature sensor may be a photodetector. The non-contact optical temperature sensor may be a pyrometer. Thermal images, thermal signatures, and/or thermal gradients may be obtained and used to determine a toilet user's body temperature. The non-contact optical temperature sensor may be used as a proximity detector and a thermal detector. The toilet may include one or more wireless transmitters or receivers. The non-contact optical temperature sensor may be a plurality of non-contact optical temperature sensors oriented such that a juxtaposition of input from the plurality of non-contact optical temperature sensors provides a complete view of events within a bowl of a toilet.

Temperature measurements may be collected continuously as excrement exits a user and falls into toilet bowl water. Temperature measurement data may be used to estimate a user's body temperature based on an average surface temperature of fecal matter leaving a user's body. The data points may all receive equal weight in the average, or data points may be weighted depending on their quality, thus yielding a more accurate estimated body temperature. The accuracy of a body temperature estimate may be presented to the user as a certainty value that indicates an accuracy of the estimated body temperature. A certainty value may be affected by length, texture, density, consistency, or circumference of the excrement. The certainty value may also be affected by the rate at which the excrement leaves the body. The certainty value may also be affected by other factors such as ambient temperature, age and cleanliness of the non-contact optical temperature sensor.

In an example, a toilet comprises an excrement-based body temperature measurement device that comprises a non-contact optical temperature sensor mounted at a rear end of the toilet bowl. The non-contact optical temperature sensor comprises a field of view that may be adjusted by the user. The non-contact optical temperature sensor may also comprise a field of measurement that may be adjusted within the bounds of the field of view. The field of measurement allows a non-contact optical temperature sensor to measure specific points of a user's excrement as it passes, and also allows it to track a user's excrement as it falls. This is particularly useful if initial readings were inconclusive.

In another example a toilet comprises an excrement-based body temperature measurement device that comprises a non-contact optical temperature sensor mounted on a toilet seat. The non-contact optical temperature sensor may be a thermal imaging sensor, a medium wavelength infrared camera, a long wavelength infrared camera, or a visible light camera. The non-contact optical temperature sensor may comprise a field of view wherein no portion of the field of view extends beyond confines of a toilet bowl comprised in the toilet and includes some or all of the water in the toilet bowl. The toilet also comprises a controller and power source. The power source may be battery power, generator power, or a wired power connection. The controller comprises one or more processors, memory, and wireless/wired transceivers for communicating data to remote computers, user devices, and remote databases. The controller is operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

BRIEF DESCRIPTION OF THE DRAWINGS

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limiting of its scope, the invention will be described and explained with additional specificity and detail through use of the accompanying drawings, in which.

DETAILED DESCRIPTION

It will be readily understood that the components of the present invention, as generally described and illustrated in the Figures herein, could be arranged and designed in a wide variety of different configurations. Thus, the following more detailed description of the embodiments of the invention, as represented in the Figures, is not intended to limit the scope of the invention, as claimed, but is merely representative of certain examples of presently contemplated embodiments in accordance with the invention. The presently described embodiments will be best understood by reference to the drawings, wherein like parts are designated by like numerals throughout.

Figure 1:
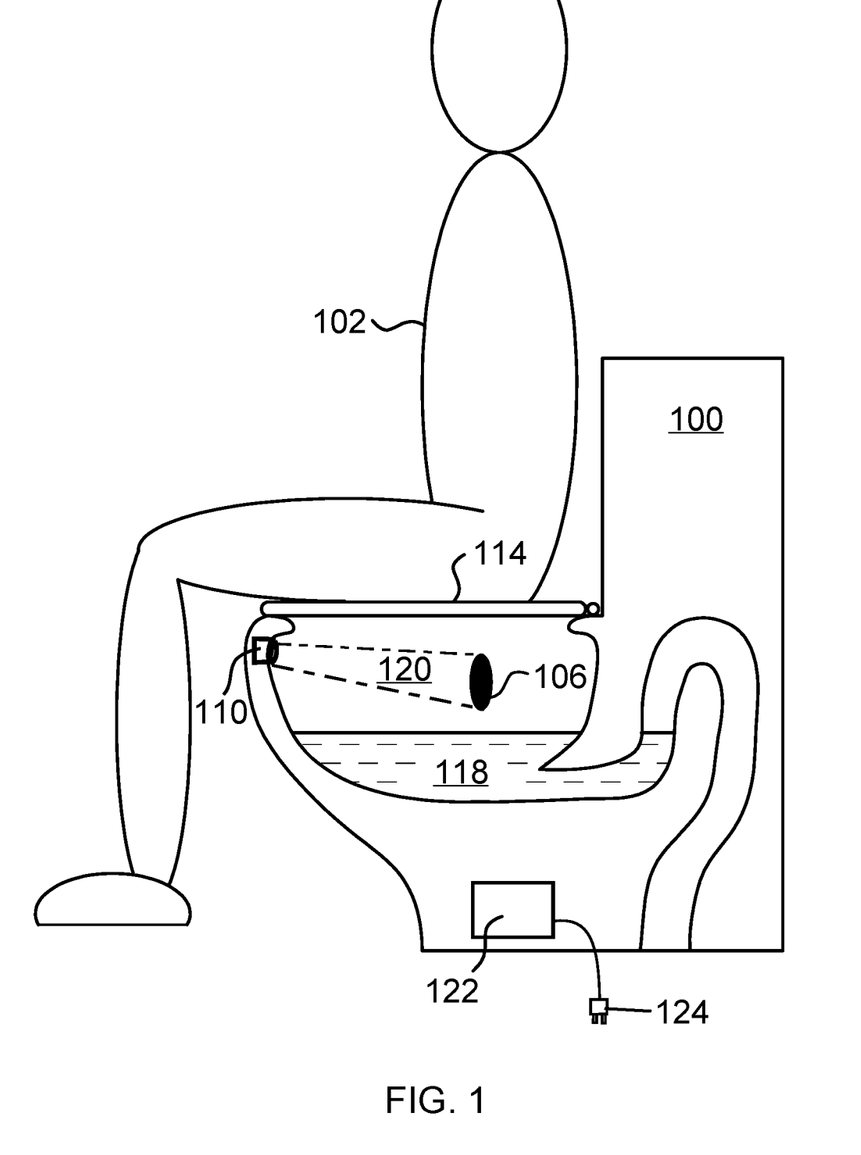
FIG. 1 shows a side cross-sectional view of the excrement-based body temperature measurement device in use.

Referring to FIG. 1, a toilet 100 comprise an excrement-based body temperature measurement device that comprises a non-contact optical temperature sensor 110. In an embodiment, the non-contact optical temperature sensor 110 may be a thermal imaging sensor, a medium wavelength infrared camera, a long wavelength infrared camera, or a visible light camera. A user 102 is shown seated on the toilet seat 114 releasing excrement 106. The non-contact optical temperature sensor 110 is mounted in such a way as to view an interior space of a toilet bowl 120 and more specifically the feces 106. Defecation events have a distinctive thermal image or thermal pattern allowing the defecation events to be distinguished from urination events. Defecation events may be compared to thermal patterns generated by one or more of the following: the toilet bowl, body parts of the toilet user, water in the toilet bowl, and/or by comparison of thermal patterns of previous elimination events. Thermal patterns of previous and instant defecation events and of urination events may be compared to each other in order to distinguish a urination event from a defecation event. The field of view of the non-contact optical temperature sensor 110 may originate on a side, front or back of toilet bowl 120 and expands outward to include water 118 and feces 106. The non-contact optical temperature sensor 110 may be oriented such that buttocks of the user 102 are not within the field of view of the non-contact optical temperature sensor 110. However, removing the buttocks of the user 102 from the field of view may negatively impact a certainty value that is generated by the body temperature measurement device as the most accurate temperatures may be acquired closes to the user's 102 anus. The field of view may also be user-adjustable to address a user's privacy concerns. Additional non-contact optical temperature sensors 110 may form an array of non-contact optical temperature sensors used to expand a field of view of an inner area of toilet 100. Additional sensors may be located in a contiguous linear sensor array or be positioned at different locations around toilet bowl 120. A body temperature of toilet user 102 may be determined by a heat signature or thermal gradient produced by feces 106 as read or detected by sensor 110 while falling from user 102 into toilet bowl water 118. A body temperature of user 103 may be obtained by an averaged or selectively averaged temperature signature or temperature gradient produced by surface area of feces 106. An area consistent temperature on the surface of the feces may be selected as useable temperature data and used to determine a body temperature of user 102. Alternatively, an instantaneous temperature reading of a portion of the feces 106 may be used to determine a body temperature of user 102.

Toilet 100 may contain a controller 122, and power source 124. Power source 124 may be battery power, generator power, or a wired power connection. Controller 122 may contain one or more processors, memory, and wireless/wired transceivers for communicating data to remote computers, user devices, and remote databases. Controller 122 may be operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 2:
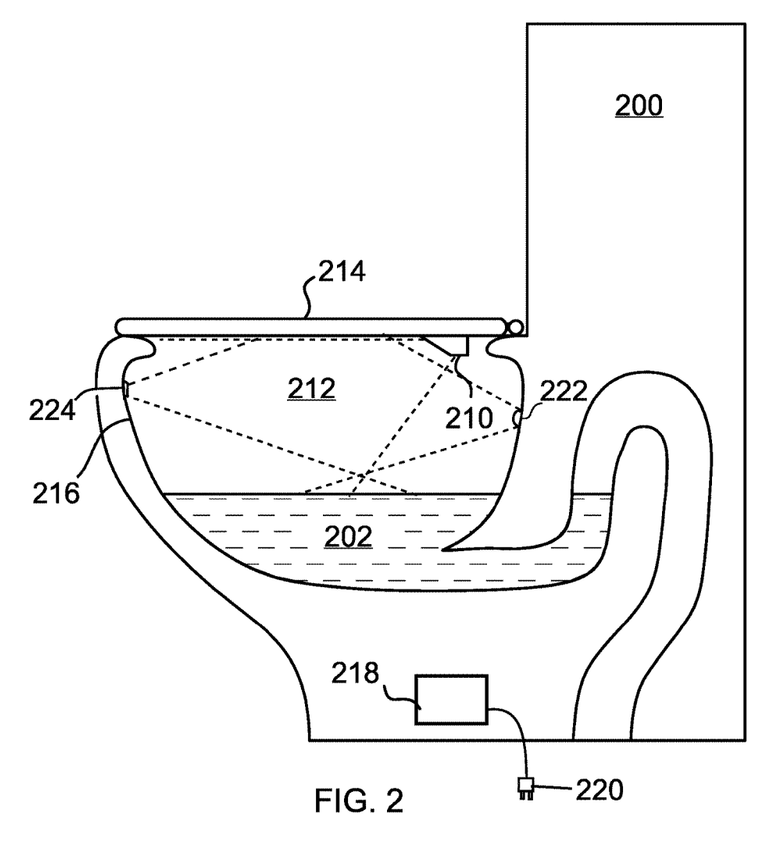
FIG. 2 shows a side cross-sectional view of the excrement-based body temperature measurement device in accordance with an embodiment of the invention.

FIG. 2 shows a toilet 200 comprising an excrement-based body temperature measurement device comprising a non-contact optical temperature sensors 210, 222, and 224. A toilet seat 214 comprises the non-contact optical temperature sensor 210. The non-contact optical temperature sensor 210 may be a thermal imaging sensor, a medium wavelength infrared camera, a long wavelength infrared camera, or a visible light camera. The sensor 210 may additionally or alternatively, work as a motion sensor or light detector. The non-contact optical temperature sensor 210 comprises a field of view 212 wherein no portion of the field of view 212 extends beyond confines of a toilet bowl 216 comprised in the toilet 200 and includes some or all of water 202 in the toilet bowl 216.

A toilet bowl 216 comprises the non-contact optical temperature sensor 224. The non-contact optical temperature sensor 224 may be a thermal imaging sensor, a medium wavelength infrared camera, a long wavelength infrared camera, or a visible light camera. The sensor 224 may additionally or alternatively, work as a motion sensor or light detector. The non-contact optical temperature sensor 224 comprises a field of view 212 wherein with a portion of the field of view 212 extending beyond the confines of a toilet bowl 216 into a perineal area of a toilet user.

A toilet bowl 216 comprises the non-contact optical temperature sensor 222. The non-contact optical temperature sensor 222 may be a thermal imaging sensor, a medium wavelength infrared camera, a long wavelength infrared camera, or a visible light camera. The sensor 222 may additionally or alternatively, work as a motion sensor or light detector. The non-contact optical temperature sensor 222 comprises a field of view 212 wherein with a portion of the field of view 212 extending beyond the confines of a toilet bowl 216 into a perineal area of a toilet user.

Non-contact temperature sensors 210, 222, and 224 may be used individually or in combination to obtain a body temperature of a toilet user. Statistical analysis may be performed on individual sensor readings and/or on combinations of sensor readings to obtain an accurate temperature of a toilet user.

Toilet 200 may contain a controller 218, and power source 220. Power source 220 may be battery power, generator power, or a wired power connection. Controller 218 may contain one or more processors, memory, and wireless/wired transceivers for communicating data to remote computers, user devices, and remote databases. Controller 218 may be operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 3:
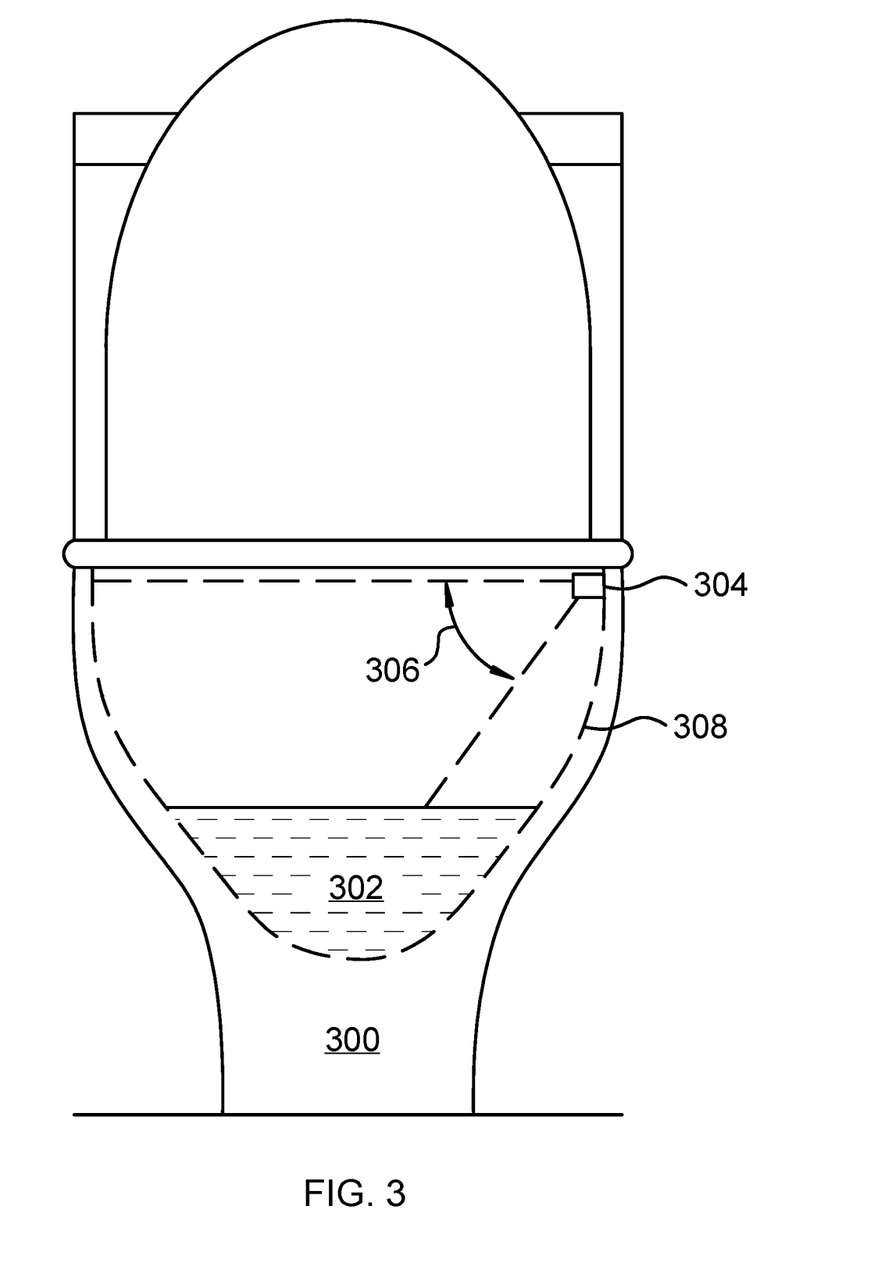
FIG. 3 is frontal cross-sectional view of the excrement-based body temperature measurement device.

FIG. 3 shows a toilet 300 comprising an excrement-based body temperature measurement device that comprises a non-contact optical temperature sensor 304 mounted in a toilet bowl 308. The non-contact optical temperature sensor 304 may be a thermal imaging sensor, a medium wavelength infrared camera, a long wavelength infrared camera, or a visible light camera. The non-contact optical temperature sensor 304 comprises a field of view 306, which is oriented on an interior side of toilet bowl 308, with an upper limit of the field of view 306 not extending outside the confines of the toilet bowl 308, and with a lower limit that includes some or all of the water 302. The non-contact optical temperature sensor 304 may be user-adjustable such that the field of view may be changed according to user preferences.

Figure 4:
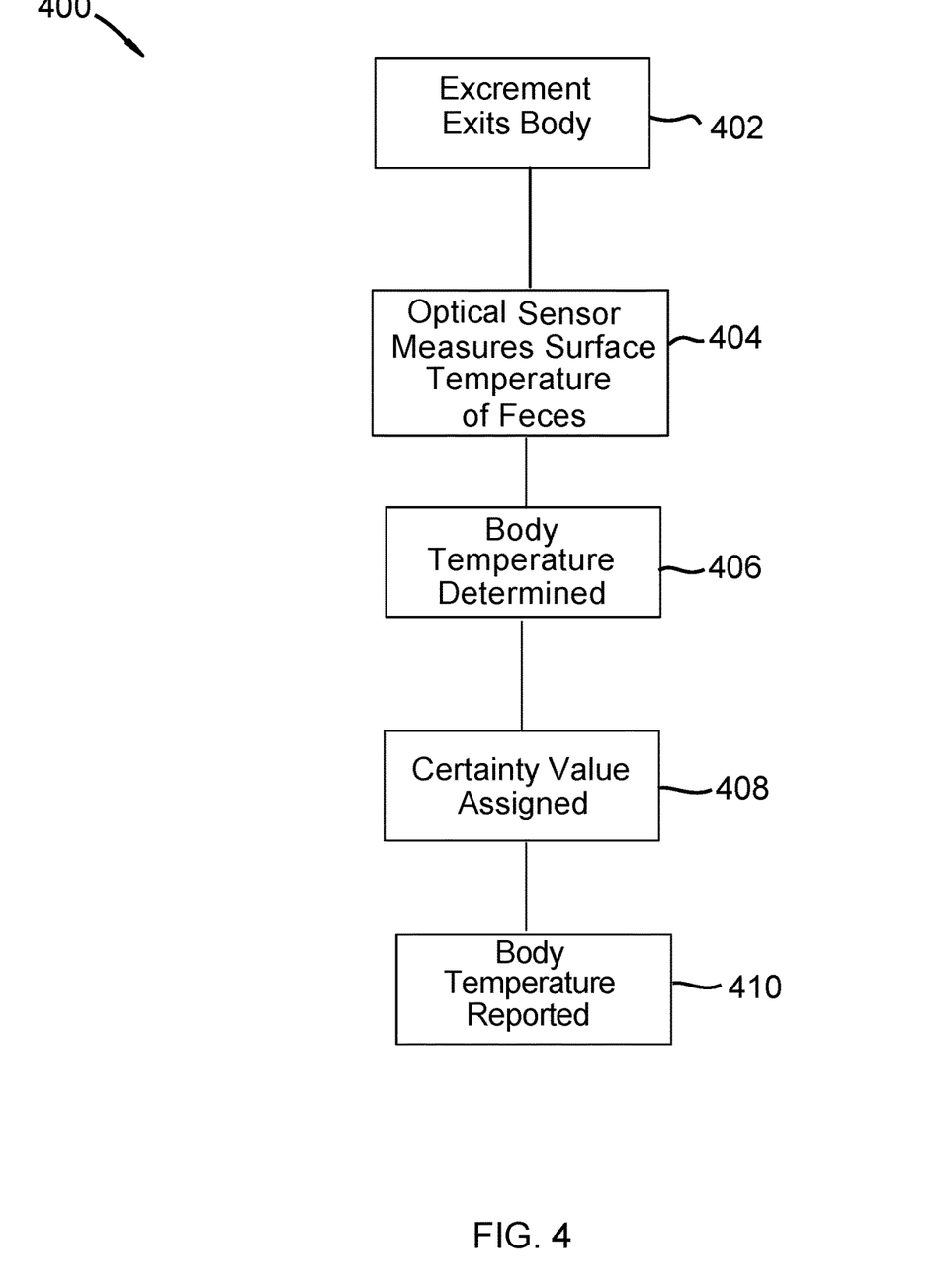
FIG. 4 charts the flow of functions in an embodiment of the excrement-based body temperature measurement device using a thermal imaging device.

FIG. 4 shows a stepwise process 400 for measuring a body temperature of a user. Excrement begins to exit a user's body in step 402, then, at step 404, a non-contact optical temperature sensor detects movement and measures a surface temperature of feces exiting the user's body or falling from the user's body into a toilet bowl. The initial measurement in step 404 may be taken as the excrement is still exiting and attached to the user or as the excrement is falling into a toilet bowl. When the non-contact optical temperature sensor observes that the excrement has completely exited the user and passed the selected point of measurement, temperature measurements cease to be gathered. In step 406, the temperatures that were collected may be averaged into a single temperature that correlates to a specific body temperature. The average temperature of the excrement may be produced by dividing the sum of the temperatures collected divided by the number of temperatures collected. The average temperature may also be determined using a weighted average where temperature measurements from later portions of the excrement carry more weight than temperature measurements from initial portions of the excrement. Greater weight may also be given to portions of excrement that are thicker, denser, or closer to a middle point of the excrement. This may be used to help increase the accuracy of an estimated body temperature that is calculated. The estimated body temperature is assigned a specific certainty value in step 408. The certainty value is based on factors observed as the excrement exits the user's body. The certainty value may be affected by length, texture, density, consistency, or circumference of the excrement. The certainty value may also be affected by the rate at which the excrement leaves the body. The certainty value may also be affected by other factors such as ambient temperature, age and cleanliness of the non-contact optical temperature sensor. In step 410 the body temperature from step 406 and the certainty value from step 408 are reported to the user. The reporting may occur by means of a display screen, a wireless transmittance to a user device, or an audio/video output.

Figure 5:
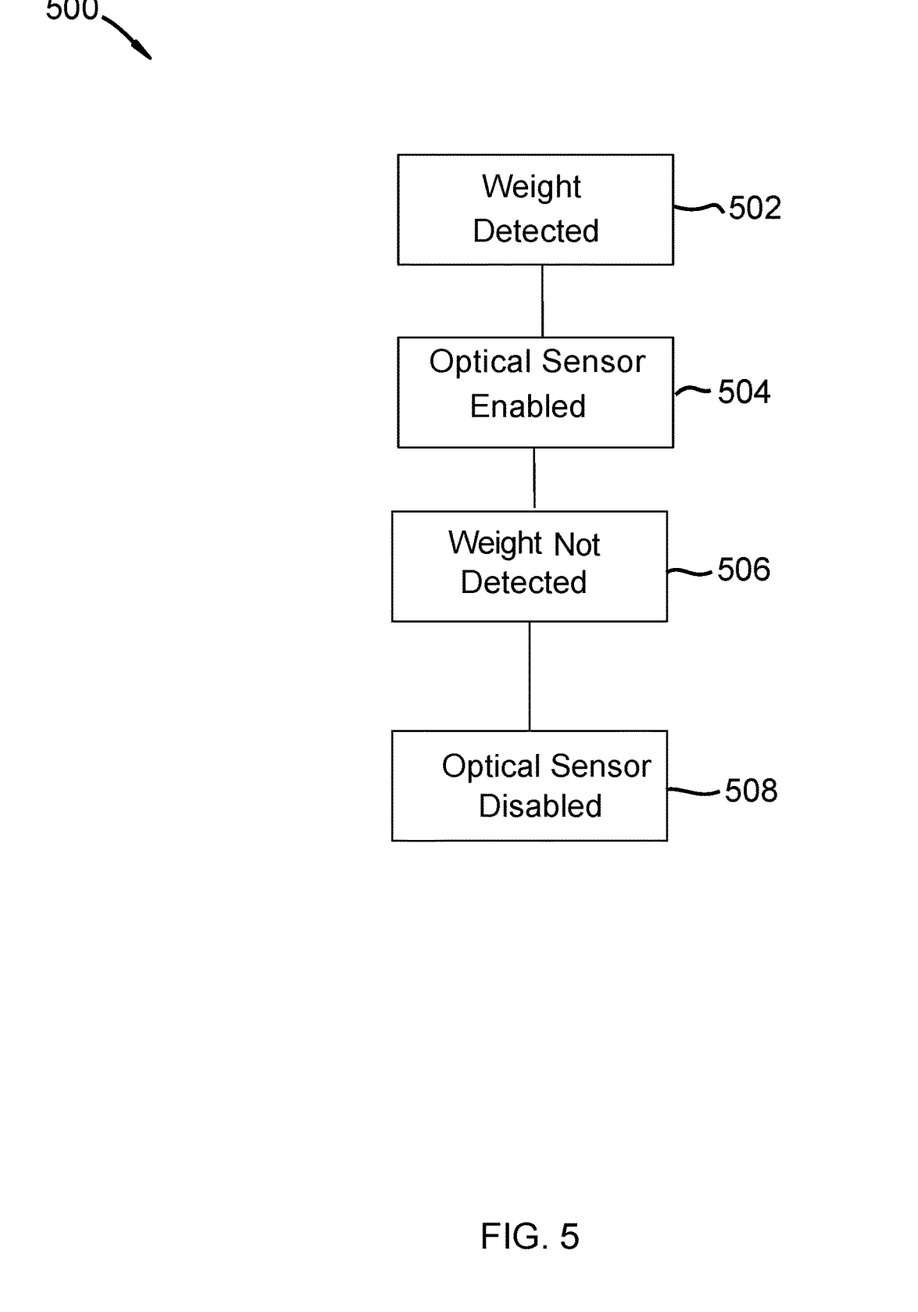
FIG. 5 charts the flow of functions in an embodiment of the excrement-based body temperature measurement device using a weight sensor.

FIG. 5 shows a stepwise method 500 for an embodiment of a body temperature apparatus wherein a strain gauge or weight sensor 502 triggers or enables a non-contact optical temperature sensor 504 to start reading temperature data within a toilet bowl when a toilet user sits on a toilet seat of a toilet. After the user is finished and weight is removed from the toilet seat at step 506 the non-contact optical temperature sensor is disabled at step 508. A strain gauge or weight sensor may provide an input to a controller within the toilet triggering the non-contact optical temperature sensor when weight is sensed on a toilet seat. When weight is removed, the non-contact optical temperature sensor may be disabled.

Figure 6:
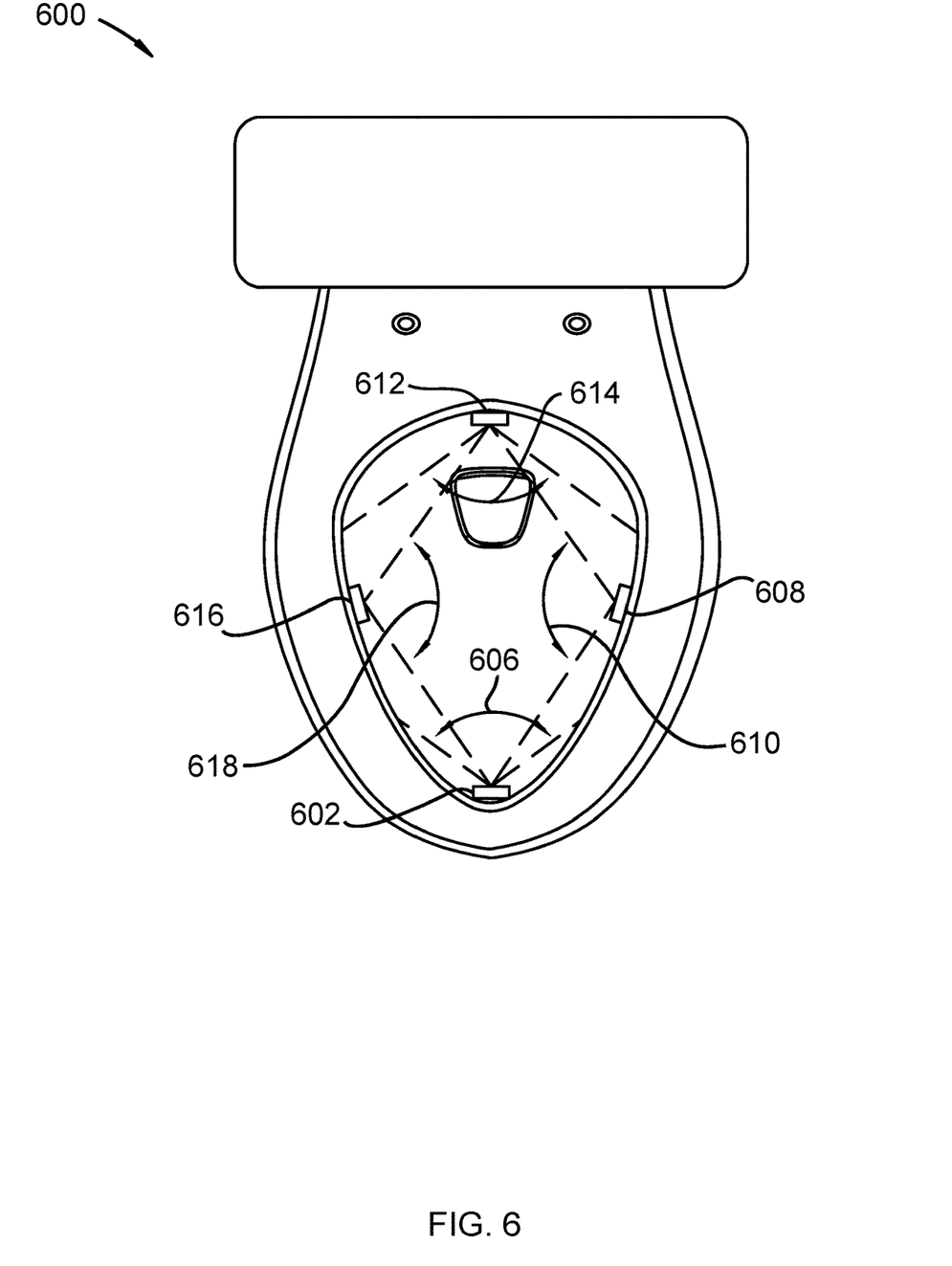
FIG. 6 is a top down view of the excrement-based body temperature measurement device.

FIG. 6 shows a top down view of toilet 600 comprising an excrement-based body temperature measurement device that comprises non-contact optical temperature sensors 602, 608, 612, and 616 that comprise fields of view 606, 610, 614, and 618 respectively. The non-contact optical temperature sensors 602, 608, 612, and 616 are mounted such that an aggregate view created by the fields of view 606, 610, 614, and 618 includes all of the interior space of the bowl of toilet 600. The aggregate view will allow for more comprehensive analysis of defecation events. The non-contact optical temperature sensors 602, 608, 612, and 616 may be any combination of thermal imaging sensors, medium wavelength infrared cameras, long wavelength infrared cameras, visible light cameras, or water level sensors. A comprehensive view of the toilet bowl may allow for volumetric measurement of human excrement, as well as create a more complete temperature profile of the excrement such that a more accurate body temperature may be estimated and/or determined.

Figure 7:
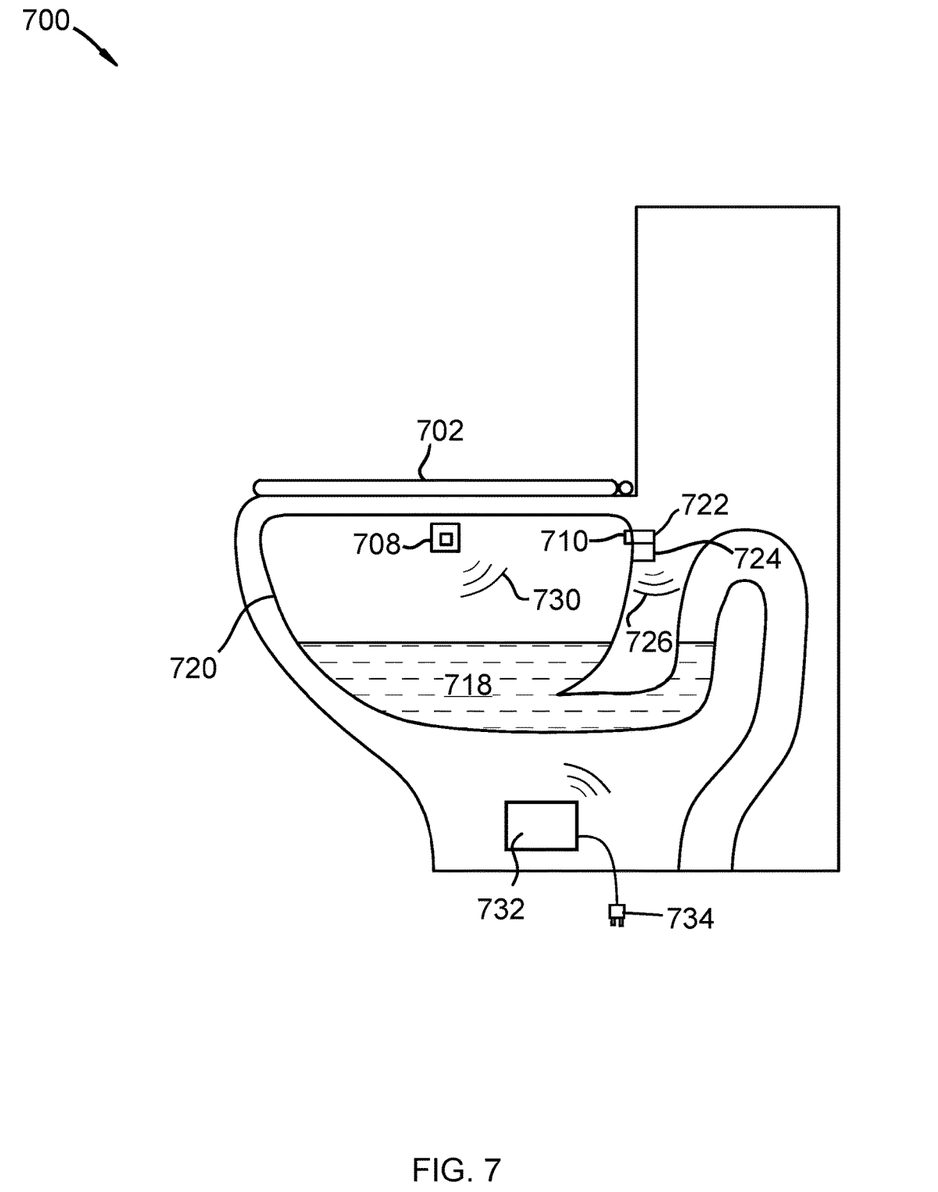
FIG. 7 is a side cross-sectional view of the excrement-based body temperature measurement device.

FIG. 7 shows a toilet 700 comprising an excrement-based body temperature measurement device that comprises a non-contact optical temperature sensor 708, a processor 722, and a wireless transceiver 724. The wireless transceiver 724 allows for wireless communication 726 and 730 such that the processor can wirelessly accept input from the non-contact optical temperature sensor 708 and perform necessary correlations and calculations. The processor 722 may be used to analyze a temperature profile of a user's excrement and may also perform the necessary calculations to produce a certainty value associated with an estimated body temperature. The processor 722 may use installed algorithms to discard irrelevant or low-quality data from an analysis.

Toilet 700 may contain a controller 732, and power source 734. Power source 734 may be battery power, generator power, or a wired power connection. Controller 732 may contain one or more processors, memory, and wireless/wired transceivers for communicating data to remote computers, user devices, and remote databases. Controller 732 may be operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 8:
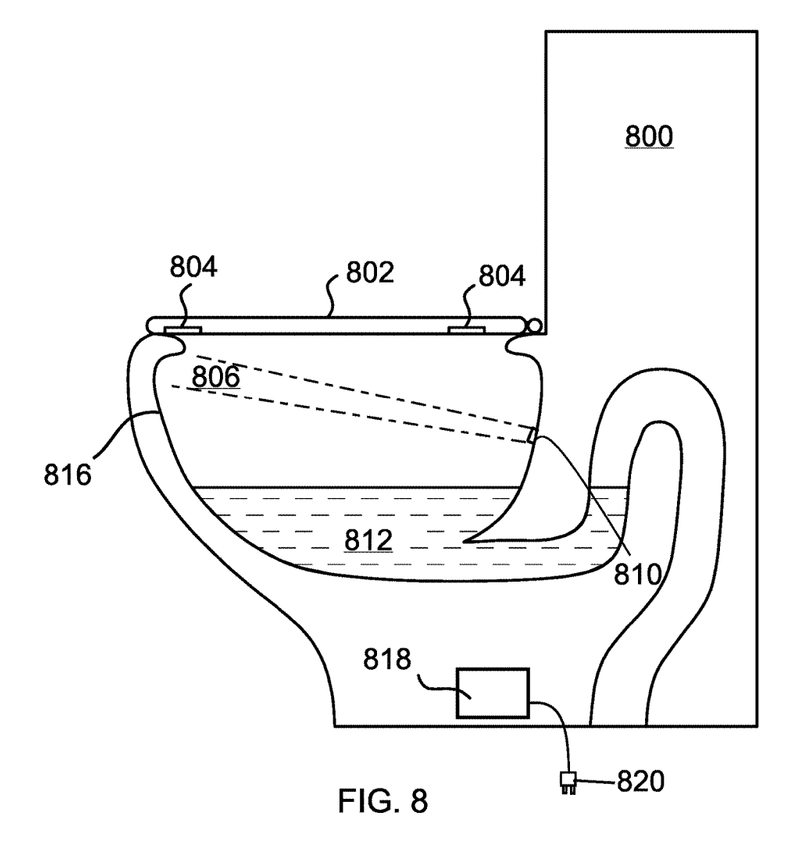
FIG. 8 is a side cross-sectional view of the excrement-based body temperature measurement device in accordance with an embodiment of the invention.

FIG. 8 shows a toilet 800 comprising an excrement-based body temperature measurement device that comprises a non-contact optical temperature sensor 810. The toilet 800 further comprises a toilet seat 802, a toilet bowl 816, and water 812. When a toilet user is sits on a toilet seat 802, strain gauges 804 may trigger non-contact optical temperature sensor 810 by way of controller 818 and begin to measure any excrement which may be released by the user into toilet bowl 816. When a toilet user releases fecal matter into toilet bowl 816 it will pass through a field of view 806 of non-contact optical temperature sensor 810. Non-contact optical temperature sensor 810 will then detect a thermal image or thermal signature of the fecal matter. The field of measurement preferably takes temperature measurements as soon as the excrement pass by field of view 806 but can track and measure any point on the surface of the excrement until the excrement enters the water 812.

Toilet 800 may contain a controller 818, and power source 820. Power source 820 may be battery power, generator power, or a wired power connection. Controller 818 may contain one or more processors, memory, and wireless/wired transceivers for communicating data to remote computers, user devices, and remote databases. Controller 818 may be operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

Figure 9:
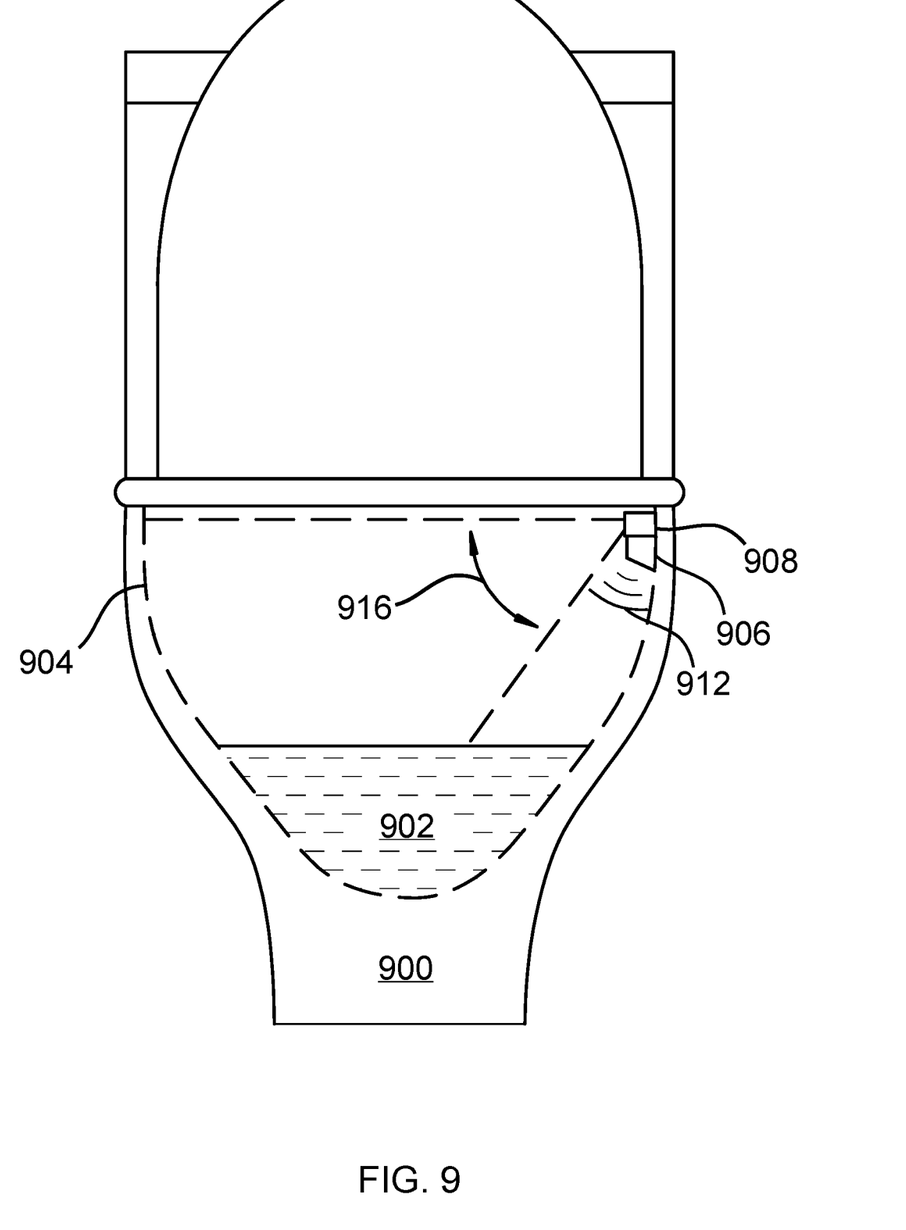
FIG. 9 is a front cross-sectional view of the excrement-based body temperature measurement device in accordance with an embodiment of the invention.

FIG. 9 shows a toilet 900 comprising a toilet bowl 904, water 902, and an excrement-based body temperature measurement device that comprises a processor 906 and a non-contact optical temperature sensor 908. The non-contact optical temperature sensor 908 comprises a field of view 916. The processor 906 comprises wireless communication capabilities 912. The processor 906 and the non-contact optical temperature sensor 908 are mounted on a side of the toilet bowl 904. The processor 906 may receive data from non-contact optical temperature sensor 908. This input may be used to estimate a user's body temperature, which then may be wirelessly transmitted to a user device, display screen, or audio output device.

Figure 10:
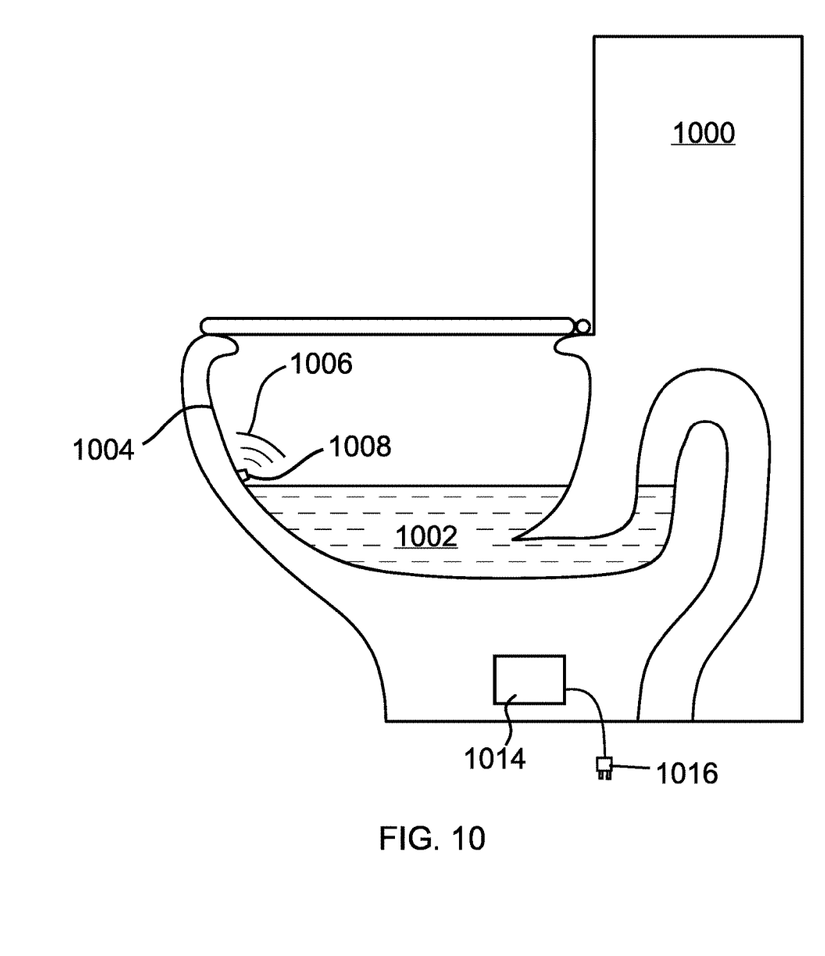
FIG. 10 is a side cross-sectional view of the excrement-based body temperature measurement device in accordance with an embodiment of the invention.

FIG. 10 shows a toilet 1000 comprising a toilet bowl 1004, water 1002, and an excrement-based body temperature measurement device that comprises a non-contact optical temperature sensor 1008. The non-contact optical temperature sensor 1008 comprises wireless communication capabilities 1006. The wireless communication capabilities 1006 may be used to transmit data and system commands to or from a user device such that a user can receive an estimate body temperature with an associated certainty value and such that a user may adjust a field of view of the non-contact optical temperature sensor 1008.

Toilet 1000 may contain a controller 1014, and power source 1016. Power source 1016 may be battery power, generator power, or a wired power connection. Controller 1014 may contain one or more processors, memory, and wireless/wired transceivers for communicating data to remote computers, user devices, and remote databases. Controller 1014 may be operably connected to one or more non-contact optical temperature sensors. A processor in the controller may be programmed to carry out data manipulation functions, data processing functions, data filtering functions, and programmed application data functions. Memory in the controller may store program data for carrying out programmed data functions. Data may be communicated over the Internet or over local networks and devices.

The systems and methods disclosed herein may be embodied in other specific forms without departing from their spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A body temperature toilet apparatus comprising:
   one or more non-contact optical temperature sensors having a field-of-view and configured to produce a measured output of the field-of-view;
   a controller configured to receive the measured output of the one or more non-contact optical temperature sensors within the field-of-view; and
   wherein based on the received output, the controller is configured to determine a body temperature of a user based on at least one of:
      a temperature of the body excrement while the body excrement is in the field-of-view of the one or more non-contact optical temperature sensors,
      a temperature of a perineal area of the user while using the toilet,
      a temperature of the body excrement while the body excrement is detached from the body and falling toward the surface of the toilet bowl, or
      a combination thereof.

2. The body temperature toilet apparatus of claim 1, wherein at least one of the non-contact optical temperature sensors is mounted under a toilet seat of a toilet.

3. The body temperature toilet apparatus of claim 2, wherein at least one of the non-contact optical temperature sensors has a field of view which is below a plane of the toilet seat.

4. The body temperature toilet apparatus of claim 1, wherein at least one of the non-contact optical temperature sensors is mounted in a toilet bowl.

5. The body temperature toilet apparatus of claim 4, wherein at least one of the non-contact optical temperature sensors has a field of view below a rim of the toilet bowl.

6. The body temperature toilet apparatus of claim 4, wherein the one or more non-contact optical temperature sensors is a plurality of non-contact optical temperature sensors oriented such that a juxtaposition of input from the plurality of non-contact optical temperature sensors provide a complete view of thermal events within the toilet bowl.

7. The body temperature toilet apparatus of claim 1, wherein at least one of the non-contact optical temperature sensors is a thermal imaging sensor.

8. The body temperature toilet apparatus of claim 1, wherein at least one of the non-contact optical temperature sensors is an infrared camera.

9. The body temperature toilet apparatus of claim 8, wherein at least one of the non-contact optical temperature sensors is a long wavelength or medium wavelength infrared camera.

10. The body temperature toilet apparatus of claim 1, wherein at least one of the non-contact optical temperature sensors is a visible light camera.

11. The body temperature toilet apparatus of claim 1, wherein the one or more non-contact optical temperature sensors is configured to continuously measure and record a plurality of temperatures of the body excrement as it exits the user at a point of exit.

12. The body temperature toilet apparatus of claim 11, wherein the controller is further configured to record the plurality of temperatures by the one or more non-contact optical temperature sensors and compile the temperatures into an evenly weighted average temperature.

13. The body temperature toilet apparatus of claim 12, further comprising one or more wireless transmitters or receivers.

14. The body temperature toilet apparatus of claim 11, wherein the controller is configured to compile recorded measurements by the one or more non-contact optical temperature sensors into a weighted average, wherein measurements closer to an initial measurement receive less weight than measurements closer to a final measurement.

15. The body temperature toilet apparatus of claim 11, wherein the controller is configured to measure the body excrement temperature at any point before the body excrement contacts the bowl water or fluid within the toilet or makes physical contact with a surface of the toilet.

16. The body temperature toilet apparatus of claim 1, wherein the controller is configured to assign a certainty value to a user's temperature measurement based on a calculated accuracy of the body temperature measurement.

17. The body temperature toilet apparatus of claim 1, wherein at least one of the non-contact optical temperature sensors is a photodetector.

18. The body temperature toilet apparatus of claim 1, wherein at least one of the non-contact optical temperature sensors is a pyrometer.

19. The body temperature toilet apparatus of claim 1, wherein the one or more non-contact optical temperature sensors comprises a proximity detector.

* * * * *